(12) United States Patent
Li et al.

(10) Patent No.: US 8,986,692 B2
(45) Date of Patent: Mar. 24, 2015

(54) ANTI-VEGF MONOCLONAL ANTIBODY AND PHARMACEUTICAL COMPOSITION COMPRISING SAID ANTIBODY

(75) Inventors: Pierre Li, Burlingame, CA (US);
Yaohuang Ke, Burlingame, CA (US);
Yongke Zhang, Burlingame, CA (US);
Weimin Zhu, Burlingame, CA (US);
Guoliang Yu, Burlingame, CA (US);
Fanxin Ma, Nanjing (CN); Xin Fan, Nanjing (CN)

(73) Assignees: Jiangsu Simcere Pharmaceutical R & D Co., Ltd., Jiangsu (CN); Apexigen Inc., Burlingame, CA (US)

( * ) Notice: Subject to any disclaimer, the term of this patent is extended or adjusted under 35 U.S.C. 154(b) by 11 days.

(21) Appl. No.: 13/393,185

(22) PCT Filed: Aug. 27, 2010

(86) PCT No.: PCT/CN2010/076420
§ 371 (c)(1),
(2), (4) Date: May 4, 2012

(87) PCT Pub. No.: WO2011/023130
PCT Pub. Date: Mar. 3, 2011

(65) Prior Publication Data
US 2012/0231011 A1 Sep. 13, 2012

(30) Foreign Application Priority Data
Aug. 28, 2009 (CN) .......................... 2009 1 0171550

(51) Int. Cl.
*A61K 39/395* (2006.01)
*C07K 16/22* (2006.01)
*A61K 39/00* (2006.01)

(52) U.S. Cl.
CPC ........... *C07K 16/22* (2013.01); *A61K 2039/505* (2013.01); *C07K 2317/24* (2013.01); *C07K 2317/565* (2013.01); *C07K 2317/76* (2013.01); *C07K 2317/92* (2013.01)
USPC .................... 424/145.1; 435/336; 530/388.23

(58) Field of Classification Search
None
See application file for complete search history.

(56) References Cited

U.S. PATENT DOCUMENTS

| 7,402,409 | B2 | 7/2008 | Yu |
| 7,429,487 | B2 | 9/2008 | Pytela et al. |
| 7,431,927 | B2 | 10/2008 | Couto et al. |
| 7,462,697 | B2 | 12/2008 | Couto et al. |
| 7,575,896 | B2 | 8/2009 | Yu |
| 7,732,168 | B2 | 6/2010 | Pytela et al. |
| 7,803,371 | B2 | 9/2010 | Ke et al. |
| 7,959,921 | B2 | 6/2011 | Couto et al. |
| 8,062,867 | B2 | 11/2011 | Pytela et al. |
| 8,071,322 | B2 | 12/2011 | Zhang |
| 8,088,375 | B2 | 1/2012 | Ke et al. |
| 8,211,433 | B2 | 7/2012 | Do Couto et al. |
| 8,293,483 | B2 | 10/2012 | Yu |
| 8,367,408 | B2 | 2/2013 | Pytela et al. |
| 8,404,816 | B2 | 3/2013 | Couto et al. |
| 8,444,984 | B2 | 5/2013 | Do Couto et al. |
| 8,617,830 | B2 | 12/2013 | Yu |
| 8,753,634 | B2 | 6/2014 | Lee et al. |
| 8,778,345 | B2 | 7/2014 | Zhang et al. |
| 2004/0086979 | A1 | 5/2004 | Zhang et al. |
| 2005/0033031 | A1 | 2/2005 | Couto |
| 2005/0048578 | A1 | 3/2005 | Zhang |
| 2005/0277127 | A1 | 12/2005 | Tian et al. |
| 2005/0287118 | A1 | 12/2005 | Tian et al. |
| 2007/0015259 | A1 | 1/2007 | Pytela et al. |
| 2010/0204059 | A1 | 8/2010 | Ke et al. |
| 2011/0008367 | A1 | 1/2011 | Ke et al. |
| 2011/0020934 | A1 | 1/2011 | Pytela et al. |
| 2012/0225060 | A1 | 9/2012 | Lee et al. |
| 2012/0231011 | A1 | 9/2012 | Li et al. |
| 2013/0130932 | A1 | 5/2013 | Yu |
| 2013/0330355 | A1 | 12/2013 | Ke et al. |
| 2014/0120103 | A1 | 5/2014 | Zhang et al. |
| 2014/0155291 | A1 | 6/2014 | Yu |
| 2014/0179556 | A1 | 6/2014 | Yu |

FOREIGN PATENT DOCUMENTS

| CN | 1445242 A | 10/2003 |
| CN | 101148474 A | 3/2008 |
| CN | 101487005 A | 7/2009 |
| JP | 2007-520991 A | 8/2007 |

(Continued)

OTHER PUBLICATIONS

Brown et al. J. Immunol. 156: 3585-3591, 1996.*
Vajdos et al. J. Mol. Biol. 320:415-428, 2002.*
Beiboer et al. J. Mol. Biol. 296: 833-849, 2000.*
Klimka et al. British J. Can. 83: 252-260, 2000.*
Zhang et al. Proceedings of the 100$^{th}$ Annual Meeting of the American Association for Cancer Research. Apr. 2009.*
Ellis et al. The Oncologist 5: 11-15, 2000.*
Extended European Search Report for European Patent Application No. 10811290.5, dated Mar. 1, 2013, 13 pages.

(Continued)

*Primary Examiner* — Christine J Saoud
(74) *Attorney, Agent, or Firm* — Seed IP Law Group PLLC

(57) ABSTRACT

The present invention provides an anti-VEGF monoclonal antibody, which has the variable region of heavy chain comprising the amino acid sequences of SEQ ID NO:1, SEQ ID NO:2 and SEQ ID NO:3, and/or the variable region of light chain comprising the amino acid sequences of SEQ ID NO:4, SEQ ID NO:5 and SEQ ID NO:6. The antibody can be produced by the cell line with the preservation number of CGMCC NO. 3233. The invention also provides the use of said antibody for the manufacture of medicaments for the treatment of a disease that is relevant to VEGF, wherein further provided are pharmaceutical composition, agents, kits and chips comprising said antibody, as well as the cell line with the preservation number of CGMCC NO. 3233.

13 Claims, 5 Drawing Sheets

(56) References Cited

FOREIGN PATENT DOCUMENTS

| JP | 2011-517447 A | 6/2011 |
|---|---|---|
| WO | 00/64946 A2 | 11/2000 |
| WO | 2004/016740 A2 | 2/2004 |
| WO | 2004/032841 A2 | 4/2004 |
| WO | 2005/007671 A2 | 1/2005 |
| WO | 2005/016950 A1 | 2/2005 |
| WO | 2006/050491 A2 | 5/2006 |
| WO | 2008/144757 A1 | 11/2008 |
| WO | 2009/120178 A1 | 10/2009 |
| WO | 2009/132037 A1 | 10/2009 |
| WO | 2011/023130 A1 | 3/2011 |
| WO | 2013/009767 A2 | 1/2013 |

OTHER PUBLICATIONS

Liang et al., "Cross-species Vascular Endothelial Growth Factor (VEGF)-blocking Antibodies Completely Inhibit the Growth of Human Tumor Xenografts and Measure the Contribution of Stromal VEGF" *The Journal of Biological Chemistry 281* (2):951-961, Jan. 13, 2006.

Yu et al., "A Humanized Anti-VEGF Rabbit Monoclonal Antibody Inhibits Angiogenesis and Blocks Tumor Growth in Xenograft Models," *PLoS ONE 52*):e9072, Feb. 2010, 12 pages.

Zhang et al., "EPI0030, a humanized anti-VEGF rabbit monoclonal antibody, exhibits potent activity in preclinical models," Abstract No. 1235, *Proceedings of the Annual Meeting of the American Association for Cancer Research*, Apr. 18-22, 2009, Denver, CO, 1 page.

Zhang et al., "EP10030, a humanized anti-VEGF rabbit monoclonal antibody, exhibits potent activity in preclinical models," *Proceedings of the American Association for Cancer Research*, 50:296 (Apr. 2009).

Spieker-Polet et al., "Rabbit monoclonal antibodies: Generating a fusion partner to produce rabbit-rabbit hybridomas," *Proc. Natl. Acad. Sci. USA*, 92:9348-9352 (Sep. 1995).

Zhang et al., "EP10030, a humanized anti-VEGF rabbit monoclonal antibody, exhibits potent activity in preclinical models," Epitomics, AACR 100th Annual Meeting, Abstract 1235, Poster Section 1M2 (13 Pages) (2009).

* cited by examiner ed with priority of the Chinese patent application No. 200910171550.9 filed on Aug. 28, 2009, entitled "Anti-VEGF Monoclonal Antibody and Pharmaceutical Composition Comprising Said Antibody," which is incorporated herein by reference in its entirety.

ANTI-VEGF MONOCLONAL ANTIBODY AND PHARMACEUTICAL COMPOSITION COMPRISING SAID ANTIBODY

The present application claims the priority of the Chinese patent application No. 200910171550.9 filed on Aug. 28, 2009, entitled "Anti-VEGF Monoclonal Antibody and Pharmaceutical Composition Comprising Said Antibody," which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 500044_402USPCa_SEQUENCE_LISTING_.txt. The text file is 18 KB, was created on May 4, 2012, and is being submitted electronically via EFS-Web.

FIELD OF THE INVENTION

The present invention relates to the technical field of genetically engineered antibodies and in particular, to genetically engineered antibodies specifically bound with the vascular endothelial growth factor (VEGF) and pharmaceutical composition and kits comprising said antibodies.

BACKGROUND OF THE INVENTION

Vascular endothelial growth factor (VEGF) is a heparin-binding growth factor specific to vascular endothelial cells, which is capable of inducing angiogenesis in vivo. Human VEGF protein was successfully purified and identified by American scientists in 1989, who also cloned and determined its gene sequence.

VEGF is capable of promoting angiogenesis. All members of the VEGF family are capable of activate cell reaction through corresponding receptors (VEGFRs) on the surface of binding cells, and are dimerized and activated through phosphorylation. VEGFRs comprise 7 immunoglobulin-like extracellular domains, one membrane-spanning domain and one intracellular domain that comprises tyrosine kinase domain. VEGF A is capable of binding with VEGF receptor 1 (receptor Flt-1) and VEGF receptor 2 (KDR/Flk-1). VEGF receptor 2 mediates almost all known biological functions of VEGF. VEGF and bioactivity and receptors thereof have been explained and studied in detail by Matsumoto et al. and Marti et al. (see Angiogenesis in ischemic disease. Thromb Haemost. 1999 Suppl 1: 44-52; VEGF receptor signal transduction Sci STKE. 2001: RE21).

VEGF is a highly conserved homodimeric glycoprotein, in which two single strands each having molecular weight of 24 kDa form the dimer through disulfide bond. Because of different ways of splicing by mRNA, at least 5 protein patterns, including VEGF 121, VEGF 145, VEGF 165, VEGF 185 and VEGF206, are developed, wherein VEGF121, VEGF 145 and VEGF 165 are secretory soluble proteins capable of directly acting on vascular endothelial cells, promoting proliferation and migration of vascular endothelial cells, and enhancing vascular permeability.

VEGF-related diseases typically have the following characteristics: over-proliferation of vascular endothelial cells, increase of vascular permeability, tissue edema and inflammation, such as cerebral edema caused by injuries, stroke or tumor; edema caused by inflammatory diseases, such as psoriasis or arthritis, including rheumatoid arthritis; asthma; anasarca associated with burns; ascites and pleural effusion caused by tumor, inflammation or trauma; chronic tracheitis; capillary leak syndrome; sapremia; kidney diseases associated with protein leakage; eye diseases, such as age-related macular degeneration and diabetic retinopathy; tumors, including breast cancer, lung cancer, colorectal cancer, brain glioma, kidney cancer, etc.

The binding between the antibody and its target spot is specific, which can mediate immunological effect mechanism and has relatively long half-life in serum. These characteristics result in strong treatment applications of the antibody.

Currently, FDA and Europe have approved the application of recombinant humanized mouse anti-VEGF monoclonal antibody, AVASTIN, in treating colorectal cancer, non-small cell lung cancer, breast cancer, brain glioma, kidney cancer and age-related macular degeneration (AMD), which reached sales of 4.8 billion US dollars in 2008. However, the AVASTIN antibody does not have a high affinity to VEGF. Because of the exclusive production, moreover, patients need to pay high prices. Currently, a patient needs to pay between about 50,000 and 100,000 US dollars per year for the drug. Therefore, there is an urgent need to develop new anti-VEGF monoclonal antibodies, thereby reducing loads on patients and lowering treatment costs.

Definitions

Prior to further description of the present invention, it is necessary to understand that the present invention is not limited by the described specific embodiments. In other words, variations may be made in specific formats. It should be further noted that since the scope of the present invention is subject to the appended claims, terms herein are only intended to describe the specific embodiments, instead of limiting the present invention.

Terms "antibody" and "immunoglobulin" may be used interchangeably herein. These terms are well known to those skilled in the art and specifically refer to proteins consisted of one or more polypeptides capable of specifically binding with antigens. One form of the antibody constitutes a basic structural unit of the antibody, which is tetramer. It consists of two pairs of completely identical antibody chains, each pair having a light chain and a heavy chain. In each pair of antibody chains, variable domains of the light chain and the heavy chain are joined together to be responsible for binding with antigens, while the constant domains are responsible for effector functions of the antibody.

Currently known immunoglobulin polypeptides comprise κ and λ light chains, and α, γ (IgG1, IgG2, IgG3, IgG4), δ, ε and μ heavy chains or other equivalents thereof. The immunoglobulin "light chain" (about 25 kDa or about 214 amino acids) in its whole length comprises a variable domain consisted of about 110 amino acids at the NH2-terminal, and a κ or λ constant domain at the COOH-terminal. Similarly, the immunoglobulin "heavy chain" (about 50 kDa or about 446 amino acids) in its whole length comprises a variable domain (about 116 amino acids) and one of heavy chain constant domains, such as γ (about 330 amino acids).

Terms "antibody" and "immunoglobulin" comprise any isoform antibodies or immunoglobulins, or antibody segments that are still specifically bound with antigens, including but not limited to Fab, Fv, scFv and Fd segments, chimeric antibody, humanized antibody, single-strand antibody, as well as fusion proteins having antigen binding portions of antibodies and non-antibody proteins. Antibodies may be labeled and detected, for example, by radioactive isotopes, enzymes capable of producing assayable substances, fluorescent proteins and biotins. Furthermore, antibodies can bind with solid carriers, including but not limited to polystyrene plates or beads. Said term further comprises Fab', Fv, F(ab')$_2$ and/or other antibody segments and monoclonal antibodies capable of specifically binding with antigens.

Antibodies may also exist in a variety of forms, for example, comprising Fv, Fab and (Fab)$_2$, as well as bifunctional hybrid antibodies (e.g., Lanzavecchia et al., Eur. J. Immunol, 1987; 17, 105), and in the form of single strand (e.g., Huston et al., Proc. NatL Acad. Sci. U.S.A., 1988; 85, 5879 and Bird et al., Science, 1988; 242, 423, which are cited herein as reference). Variable domains of heavy chain or light chain of immunoglobulin consist of three hypervariable domains (also referred to as "complementarity determining region" or CDR). These hypervariable domains are spaced apart by framework regions (FR). The scopes of FR and CDR have been precisely defined (see "Sequences of Proteins of Immunological Interest," E. Kabat et al., U.S. Department of Health and Human Services, 1991). Amino acid sequences of all antibodies discussed herein are sorted by referring to the Kabat system. Different light chain and heavy chain FR sequences of the same species are relatively conserved. Antibody FRs are used to position and calibrate CDRs. CDRs are mainly responsible for binding with antigen epitopes.

A chimeric antibody is an antibody with constructed heavy chain and light chain genes, in particular an antibody with variable domain and constant domain genes that are genetically engineered and belong to different species. For example, variable domain segments of mouse monoclonal antibody genes are joined to constant domain segments of human antibody, such as γ1 and γ3. For example, chimeric antibodies used in medical treatment are a type of chimeric proteins, which are rabbit antibody variable domain segments or antigen binding domain segments combined with human antibody constant domains or effect domains (e.g. the anti-Tac chimeric antibody prepared with the cell deposited under the accession number of A.T.C.C. No. CRL 9688). Of course, chimeric antibodies can also use genes from other mammal species.

Terms "humanized antibody" and "humanized immunoglobulin" have the same meaning. Compared with the non-humanized form of an antibody, its humanized antibody typically reduces the immunoreaction in the human host.

It should be understood that the humanized antibody designed and produced according to the present invention may replace some conservative amino acids, which have substantially no impact on antigen binding or other functions of the antibody. In other words, amino acids can be mutually substituted in the combinations of gly and ala; val, ile and leu; asp and glu; asn and gln; ser and thr; lys and arg; phe and tyr. Amino acids not in the same group are "substantially different" amino acids.

In some embodiments, the affinity between an antibody and its target spot is represented by $K_d$ (dissociation constant), which is lower than $10^{-6}$ M, $10^{-7}$ M, $10^{-8}$ M, $10^{-9}$ M, $10^{-10}$ M, $10^{-11}$ M or about $10^{-12}$ M or lower.

"Variable domain" of an antibody's heavy chain or light chain is the mature region at the N terminal of said chain. All domains, CDRs and residue numbers are defined through sequence alignment and based on existing structural knowledge. Determination and numbering of FR and CDR residues are based on what Chothia and others have described (Chothia, Structural determinants in the sequences of immunoglobulin variable domain. J Mol Biol. 1998; 278, 457).

VH is the variable domain of the antibody's heavy chain. VL is the variable domain of the antibody's light chain, which may comprise κ and λ isotypes. K-1 antibody has the κ-1 isotype, while K-2 antibody has the κ-2 isotype, and Vλ is the variable λ light chain.

Terms "polypeptide" and "protein" may be used interchangeably herein. Both of them refer to polymerized amino acids of any length, which may comprise encoding and non-encoding amino acids, chemically or biochemically modified or derived amino acids and polypeptides having modified peptide skeletons. Said terms comprise fusion proteins, including but not limited to fusion proteins having heterogeneous amino acid sequences; fusion proteins having heterogeneous and homogeneous leader sequences, with or without N-terminal methionine residues; proteins with immunological tags; fusion proteins with detectable fusion partners, for example, fusion proteins that can function as fusion partners, including fluorescent protein, β-galactosidase, fluorescein, etc. Polypeptides can be of any length, and the term "peptide" refers to polypeptides of the length of 8-50 residues (e.g. 8-20 residues).

Terms, "subject", "host", "patient" and "individual", may be used interchangeably herein, and specifically refer to any mammals, in particularly humans, that are diagnosed or treated. Other subjects may comprise monkey, cow, dog, cat, Guinea pig, rabbit, rat, mouse, horse, etc.

"Corresponding amino acids" refer to amino acid residues at the same positions (i.e. they correspond to each other) when two or more amino acid sequences are compared. Comparison and numbering methods of antibody sequences have been described in detail by Chothia (see above), Kabat (see above), and others. It is known to those skilled in the art (see, for example, Kabat 1991 Sequences of Proteins of Immunological Interest, DHHS, Washington, D.C.) that sometimes one, two or three gaps may be made, and/or 1, 2, 3 or 4 residues or at most about 15 residues (in particular in L3 and H3 CDRs) may be inserted in one or two amino acids of an antibody, thereby completing a comparison.

"Substitutable position" refers to a special position of an antibody, which can be substituted by different amino acids without significantly reducing the antibody's binding activity. Methods to determine substitutable positions and how they can be substituted will be described below in more detail. The substitutable position may also be referred to as "variation tolerant position".

"Parent" antibody refers to the target antibody of amino acid substitution. In some embodiments, a "donor" antibody will "donate" amino acids to a parent antibody to produce a changed antibody. "Associated antibody" refers to an antibody having similar sequence and produced by cells having the common B cell ancestor. This B cell ancestor comprises genome that has rearranged light chain VJC domains and rearranged heavy chain VDJC domains, and moreover, produces antibodies that have not experienced affinity maturation. The "naive" or "primary" B cell that exists in the spleen tissue is the common ancestor of B cells. The bindings of associated antibodies with an identical epitope are typically very similar in sequence, in particular their L3 and H3 CDRs. All H3 and L3 CDRs of associated antibodies have the same length and nearly identical sequence (with 0-4 different amino acid residues). Associated antibodies are correlated through the common antibody ancestor, i.e. the antibody produced by the original B cell ancestor.

SUMMARY OF THE INVENTION

The object of the present invention is to provide a monoclonal antibody having higher affinity with VEGF. The VEGF monoclonal antibody according to the present invention has the variable domain of heavy chain comprising amino acid sequences of SEQ ID NO: 1, SEQ ID NO: 2 and SEQ ID NO: 3, and/or the variable domain of light chain comprising amino acid sequences of SEQ ID NO: 4, SEQ ID NO: 5 and SEQ ID NO: 6.

The "antibody" herein shall be interpreted as encompassing any specific binding factors having the binding domain with required specificity. Therefore, this term encompasses homogeneous antibody segments, derivatives, and humanized antibodies thereof, as well as the antibody's functional equivalents and homologues, and also includes any polypeptide having antigen binding domains, either natural or synthetic. Examples of the antibody are immunoglobulin subtypes (e.g. IgG, IgE, IgM, IgD and IgA) and subtypes and subclasses thereof; it may further be a segment comprising antigen binding domains, such as Fab, scFv, Fv, dAb and Fd; and diabodies. Chimeric molecules fused to another polypeptide and comprising antigen binding domain or equivalents thereof are also included. Cloning and expression of chimeric antibodies are described in EP. A-0120694 and EP. A. 0125023.

The monoclonal antibody according to the present invention may be, for example, monovalent or single-strand antibody, double-strand antibody, chimeric antibody, humanized antibody, and derivatives, functional equivalents and homologues of the above antibodies, and may further comprise antibody segments and any polypeptide comprising antigen binding domains.

Antibodies may be modified through a variety of ways, may produce other antibodies or chimeric molecules that retain the original antibody's specificity using the DNA recombinant technology. This technology may introduce DNA that encodes immunoglobulin variable domains or CDRs of the antibody into constant domains or constant domains plus framework regions of different immunoglobulins. See EP. A. 184187, GB 2188638A or EP. A. 239400. Genetic mutation or other changes may be performed on hybridoma or other cells that produce antibodies, which may change or not change the binding specificity of the produced antibodies.

Other than highly variable domains CDR1, CDR2 and CDR3 in heavy chains and light chains, and linker sequences, the remaining part of the monoclonal antibody according to the present invention is framework region. The framework region may be replaced by other sequences provided that the three dimensional structure required by the binding is not affected. The molecular basis of the antibody's specificity primarily comes from its highly variable domains CDR1, CDR2 and CDR3, which are key positions to bind with antigens. To maintain the preferred binding specificity, CDRs' sequences should be retained as much as possible. However, it might be necessary to change some amino acids to optimize the binding specificity. Those skilled in the art may attain this goal through standard practices.

In some preferred embodiments, a monoclonal antibody comprises variable domains as follows: a heavy chain variable domain comprising, for example, SEQ ID NO: 7, which comprises CDR1 (SNNDVMCW; SEQ ID NO: 1), CDR2 (GCIMTTDVVTEYANWAKS; SEQ ID NO. 2) and CDR3 (RDSVGSPLMSFDLW; SEQ ID NO: 3); and a light chain variable domain comprising, for example, SEQ ID NO: 8, which comprises CDR1 (QASQSIYNNNELS; SEQ ID NO: 4), CDR2 (RASTLAS; SEQ ID NO: 5), and CDR3 (GGYKSYSNDGNG; SEQ ID NO: 6).

Except for the difference in substitution of at most 6 amino acids, variants of variable domains CDRs are substantially the same as the above CDRs (e.g., substitution of 1, 2, 3, 4, or 5 amino acids), and CDRs of said monoclonal antibody have VEGF binding activities.

In other embodiments, the antibody may comprise: a) a heavy chain variable domain, whose amino acid sequence is different from SEQ ID NO: 7 in having at most 6 amino acid substitutions, for example, 1, 2, 3, 4, 5 or 6 amino acid substitutions; and b) a light chain variable domain, whose amino acid sequence is different from SEQ ID NO: 8 in having at most 6 amino acid substitutions, for example, 1, 2, 3, 4, 5 or 6 amino acid substitutions. The target antibody may comprise any one of these substitutions or combinations thereof.

Similarly, the antibody that has any one of these substitution positions and the antibody that has all substitution positions have VEGF-binding activities. Amino acid substitutions may exist in framework regions and CDRs simultaneously, or independently appear in framework regions or CDRs. In some preferred embodiments, therefore, amino acid sequences of the framework regions of the heavy chain variable domain may be different from SEQ ID NO: 7 in having at most 6 amino acid substitutions, for example, 1, 2, 3, 4, 5 or 6 amino acid substitutions, and amino acid sequences of the framework regions of the light chain variable domains may be different from SEQ ID NO: 8 in having at most 6 amino acid substitutions, for example, 1, 2, 3, 4, 5 or 6 amino acid substitutions.

In some antibodies, amino acid substitution may spread in a plurality of CDRs. Therefore, amino acid sequences of a plurality of CDRs of the heavy chain variable domains may be different from SEQ ID NO: 7 in having at most 6 amino acid substitutions, for example, 1, 2, 3, 4, 5 or 6 amino acid substitutions, and amino acid sequences of a plurality of CDRs of the light chain variable domains may be different from SEQ ID NO: 8 in having at most 6 amino acid substitutions, for example, 1, 2, 3, 4, 5 or 6 amino acid substitutions.

In a special preferred embodiment, the antibody may comprise a) a heavy chain variable domain, whose amino acid sequence is the same as SEQ ID NO: 7, and b) a light chain variable domain, whose amino acid sequence is the same as SEQ ID NO: 8.

In a special preferred embodiment, the antibody may comprise a) a heavy chain variable domain, whose amino acid sequence has at least 95% identity with SEQ ID NO: 7, and b) a light chain variable domain, whose amino acid sequence has at least 95% identity with SEQ ID NO: 8. Therefore, the target antibody may comprise a) a heavy chain variable domain, whose amino acid sequence has at least about 95%, 96%, 97%, 98%, 99% or 100% identity with SEQ ID NO: 7, and b) a light chain variable domain, whose amino acid sequence has at least about 95%, 96%, 97%, 98%, 99% or 100% identity with SEQ ID NO: 8.

In a special preferred embodiment, the antibody may comprise a) a heavy chain, whose amino acid sequence is the same as SEQ ID NO: 9, and b) a light chain, whose amino acid sequence is the same as SEQ ID NO: 10.

In a special preferred embodiment, the antibody may comprise a) a heavy chain, whose amino acid sequence has at least 95% identity with SEQ ID NO: 9, and b) a light chain, whose amino acid sequence has at least 95% identity with SEQ ID NO: 10. Therefore, the target antibody may comprise a) a heavy chain, whose amino acid sequence has at least about 95%, 96%, 97%, 98%, 99% or 100% identity with SEQ ID NO: 9, and b) a light chain, whose amino acid sequence has at least about 95%, 96%, 97%, 98%, 99% or 100% identity with SEQ ID NO: 10. In addition to the above described amino acid substitutions, the target antibody may have additional amino acids at both ends of the heavy chain or light chain. For example, the target antibody may comprise at least 1, 2, 3, 4, 5 or 6 or more additional amino acids at C or N terminal of the heavy chain and/or light chain, respectively. In some embodiments, the target antibody may be shorter than exemplary amino acids described herein, the primary difference thereof being that the two ends of the heavy chain and the light chain have 1, 2, 3, 4, 5 or 6 amino acids less than the exemplary amino acids, respectively.

The target antibody may be humanized. Generally speaking, the humanized antibody is an antibody modified through performing amino acid substitution in the framework region of the parent antibody, and compared with the parent antibody, the humanized antibody has lower immunogenicity. Antibodies may be humanized with a number of technologies that are well known in the art, including, such as CDR transplant (ERA-239, 400; PCT publication WO 91/09967; U.S. Pat. Nos. 5,225,539; 5,530,101; and 5,585,089) and chain shuffling (U.S. Pat. No. 5,565,332). In some preferred embodiments, framework replacement determines the importance of framework residues in antigen binding through simulating the interaction between CDRs and framework residues and identifies unusual framework residues through sequence alignment (see, for example, U.S. Pat. No. 5,585,089; Riechmann, et al., Nature, 1988; 332, 323). Refer to the U.S. patent application Ser. No. 10/984,473 filed on Nov. 8, 2004 and entitled "Methods for antibody engineering" for specific details of the antibody humanization method. Said application has been incorporated herein in its entirety as reference. Generally speaking, such humanization methods comprise the identification of appropriate sites through comparing antibody sequences capable of binding identical antigens, and substitution of amino acids on said sites with different amino acids at the same sites of similar amino acids. According to these methods, amino acid sequences of the parent antibody are compared with other associated antibodies (e.g. sequence alignment), thereby identifying variation tolerant positions. Amino acid sequences of variable domains of the parent antibody are typically compared with amino acid sequences in human antibody databases, and a humanized antibody with similar amino acid sequences as the parent antibody is selected. Sequences of the parent antibody and the humanized antibody are compared (e.g. sequence alignment), and amino acids at one or more variation tolerant positions of the parent antibody are substituted by amino acids at corresponding positions in the humanized antibody.

The above-discussed substitution method of variation tolerant positions can be easily combined with any known humanization method, and be easily applied in the production of humanized antibodies comprising CDRs, the CDRs of said antibodies being modified while loyal to the CDR of the parent antibody. Therefore, the present invention further provides humanized VEGF-neutralizing antibodies comprising a plurality of CDRs from the modified versions of the parent antibody.

Compared with AVASTIN, a product according to the prior art, the humanized rabbit anti-VEGF monoclonal antibody according to the present invention has a lower dissociation constant Kd (the monoclonal antibody according to the present invention has a Kd of 0.485 nM, while that of AVASTIN is 47.9 nM), the monoclonal antibody according to the present invention has higher affinity with VEGF, indicating that the present invention has stronger inhibition on VEGF. Experiments with mouse models have shown that the antibody according to the present invention has a noticeably higher tumor inhibition rate than AVASTIN (see Example 5).

Therefore, the present invention has theoretically higher potential clinical healing effect than AVASTIN.

In an embodiment, the monoclonal antibody according to the present invention is produced by the cell line deposited under the accession number CGMCC No. 3233, with its heavy chain amino acid sequence shown by SEQ ID NO: 9 and its light chain amino acid sequence shown by SEQ ID NO: 10. Its dissociation constant with VEGF is 0.485 nM, which is 1/100 of that of AVASTIN, showing that EPI0030 has a stronger binding capability with VEGF than AVASTIN does.

The present invention further provides a cell line, which is deposited in the China General Microbiological Culture Collection Center under the accession number of CGMCC No. 3233. It produces a monoclonal antibody, said antibody having a heavy chain amino acid sequence shown as SEQ ID NO: 9 and a light chain amino acid sequence shown as SEQ ID NO: 10. In embodiments according to the present invention, it is named as EPI0030 antibody. Cell experiments and in vivo animal experiments have shown that it is capable of in vitro inhibition of the proliferation and migration of endothelial cells induced by VEGF, and can inhibit tumor growth inside animal body. It can be used to treat VEGF-associated diseases.

The present invention further provides the application of said monoclonal antibody in preparing drugs to treat VEGF-associated diseases. Said VEGF-associated diseases include tumors, AMD, neurodegenerative diseases, obesity, and diabetes. Said target antibody may be used in VEGF-associated studies, such as studies in a variety of fields, including development biology, cytobiology, metabolism, structure biology, and functional genomics, or applicable medical and pharmaceutical studies on tumors, AMD, neurodegenerative diseases, obesity, and diabetes, etc.

The present invention further provides a pharmaceutical composition, characterized in that it comprises an effective amount of the above monoclonal antibody and a pharmaceutically acceptable carrier.

The present invention further provides a reagent, kit or chip comprising the above monoclonal antibody.

The present invention further provides a method of using the target antibody to inhibit the VEGF activity and using the target antibody to treat VEGF-associated diseases or using a kit containing said antibody to perform VEGF-associated diagnosis and assay.

When the antibody molecule according to the present invention is prepared, it can be purified with any known method in the art for purifying immunoglobulin molecules, for example, chromatography (for example, ion exchange chromatography, affinity chromatography, in particular the affinity chromatography for specific antigens through protein A, and other column chromatography), centrifuge, solubility difference, or any other standard techniques for purifying proteins. In many embodiments, the antibody is secreted from cells into the culture medium, and the antibody is obtained through collecting the culture medium and purification.

The antibody may be modified through a variety of ways, may produce other antibodies or chimeric molecules that retain the original antibody's specificity using the DNA recombinant technology. This technology may introduce DNA that encodes immunoglobulin variable domains or CDRs of the antibody into constant domains or constant domains plus framework regions of different immunoglobulins. See EP. A. 184187, GB 2188638A or EP. A. 239400. Genetic mutation or other changes may also be performed on hybridoma or other cells that produce antibodies, which may change or not change the binding specificity of the produced antibodies.

The monoclonal antibody used in the present invention may also be prepared with the hybridoma method. Since the DNA sequence that codes the humanized antibody according to the present invention can be obtained through a conventional means known to those skilled in the art, such as the artificial synthesis of amino acid sequences publicized in the present invention or the PCR amplification, therefore, said sequence can also be linked into an appropriate expression carrier with the recombinant DNA method and with a variety of methods known in the art. Finally, under conditions suitable for the expression of the antibody according to the present invention, cultivate and transform the obtained host cell, and then those skilled in the art employ a well-known conventional separation and purification means to purify the monoclonal antibody according to the present invention.

As described above, the present invention further provides reagents, kits or chips for carrying out the antibody according to the present invention. The reagents, kits or chips at least comprise the following one or more: the antibody prepared according to the above method, ribonucleotide that encodes said antibody, or eukaryotes cells, prokaryocytic cells and viruses that contain said antibody. The antibody can be humanized.

Other optional components of the reagents, kits or chips comprise: restriction endonuclease, primer and plasmid, buffer solution, etc. for conducting experiments of antibody activity assay. Nucleic acids of said reagents, kits or chips may further comprise restriction endonuclease sites, multiple clone sites, primer sites, etc. for connection thereof with non-rabbit antibody nucleic acids. All components of said agents, kits or chips may be stored individually in separate containers, or some compatible components may be pre-assembled into a single container as needed.

Pharmaceutically accepted carriers may be added when preparing the target antibody. Term "pharmaceutically accepted carrier" refers to one or more organic or inorganic ingredients, which may be natural or synthetic and can promote the application of the antibody after combining with the antibody. Pharmaceutically accepted carriers comprise sterile saline solution or other aqueous or non-aqueous isosmotic solutions and sterile suspensions that are pharmaceutically available and known in the art. "Effective dosage" refers to the dosage that can improve or postpone the progress of pathologic, degenerative or damaged situations.

The definition of the effective dosage is individually based, specifically, it considers treatment of symptoms and to look for results based on individuals. The effective dosage is determined through a common technique in the art, and these factors to use the same will not exceed conventional experiments.

Description of Biological Material Deposition

The cell line with the accession number of CGMCC NO. 3233 was deposited on Aug. 20, 2009 in CGMCC with the address at Datun Road, Chaoyang District, Beijing, under the term of the Budapest Treaty, and its classification name is Chinese hamster ovarian cell.

Figure 3:
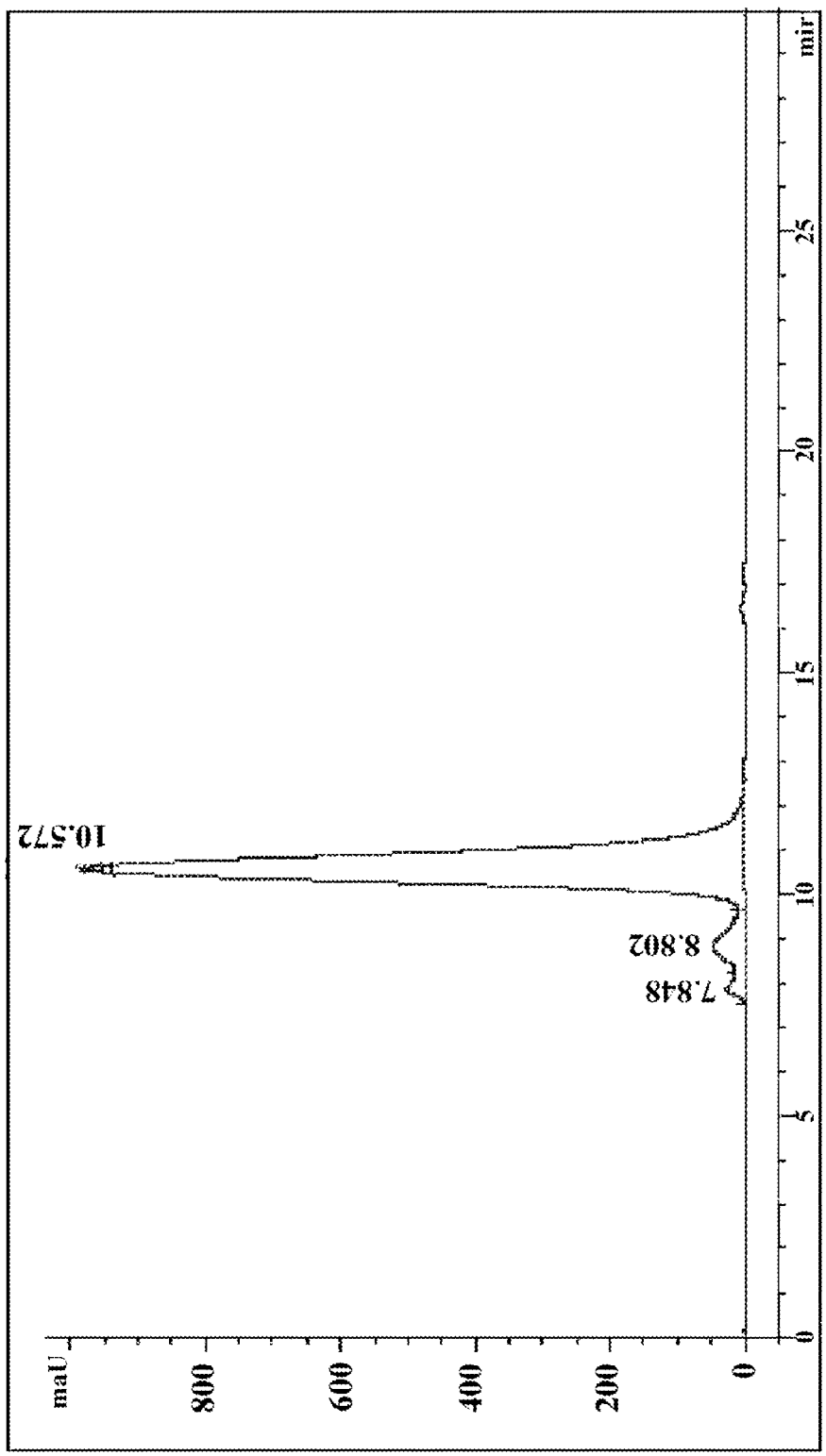
Figure 4:
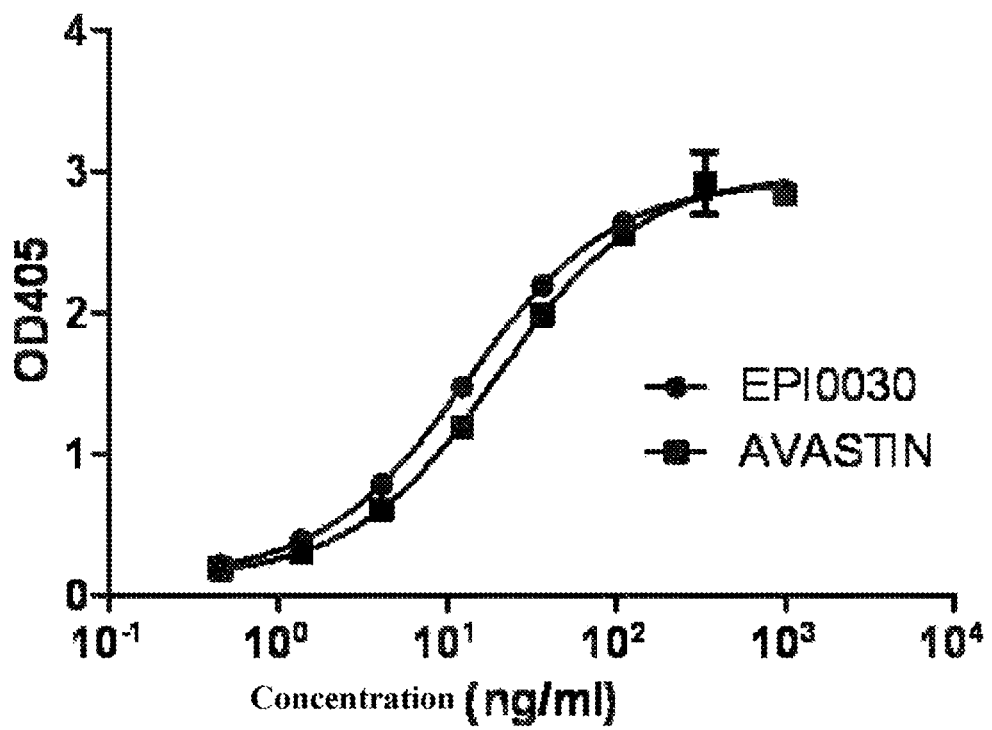
Figure 5:
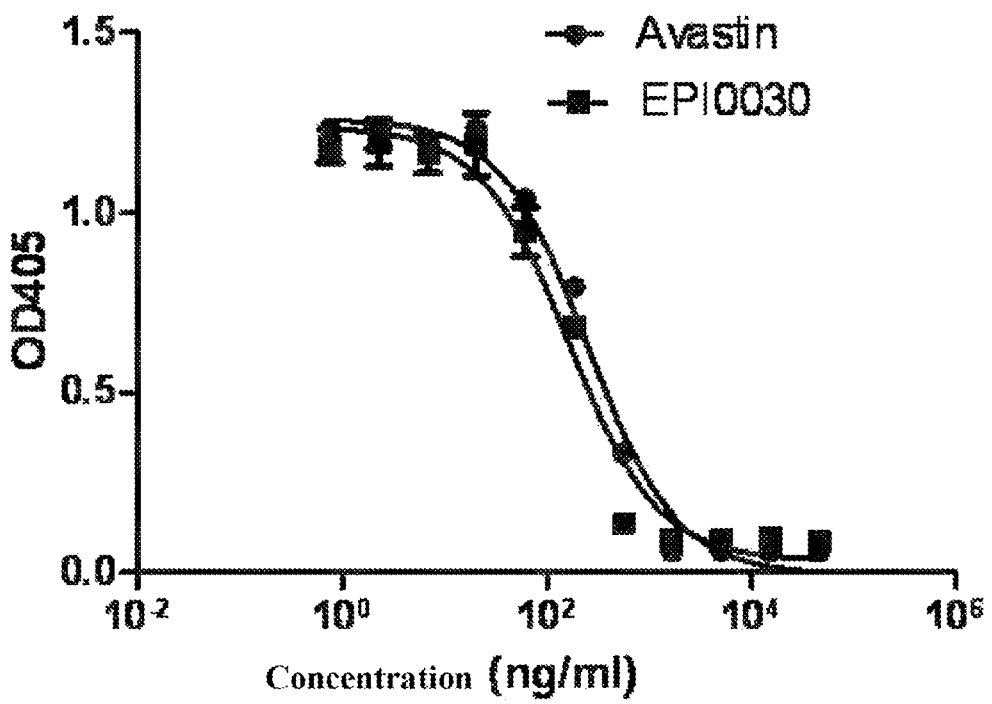

Lane 1 is reducing electrophoresis;

Lane 2 shows molecular weight standards—sequentially from above down, 170 kD, 130 kD, 100 kD, 70 kD, 55 kD, 40 kD, 35 kD, 25 kD, 15 kD and 10 kD;

Lane 3 is non-reducing electrophoresis;

FIG. 3 shows the SEC-HPLC analysis graph of the purity of EPI0030 antibody expressed by the HZD-V6 clone;

FIG. 4 shows the binding activity of the antibody with human VEGF determined using the VEGF direct binding method;

FIG. 5 shows the $IC_{50}$ assay of inhibition of the binding of VEGF and KDR by EPI0030 and AVASTIN;

EPI0030's $IC_{50}$=166.3 ng/ml, AVASTIN's $IC_{50}$=253.7 ng/ml.

Figure 6:
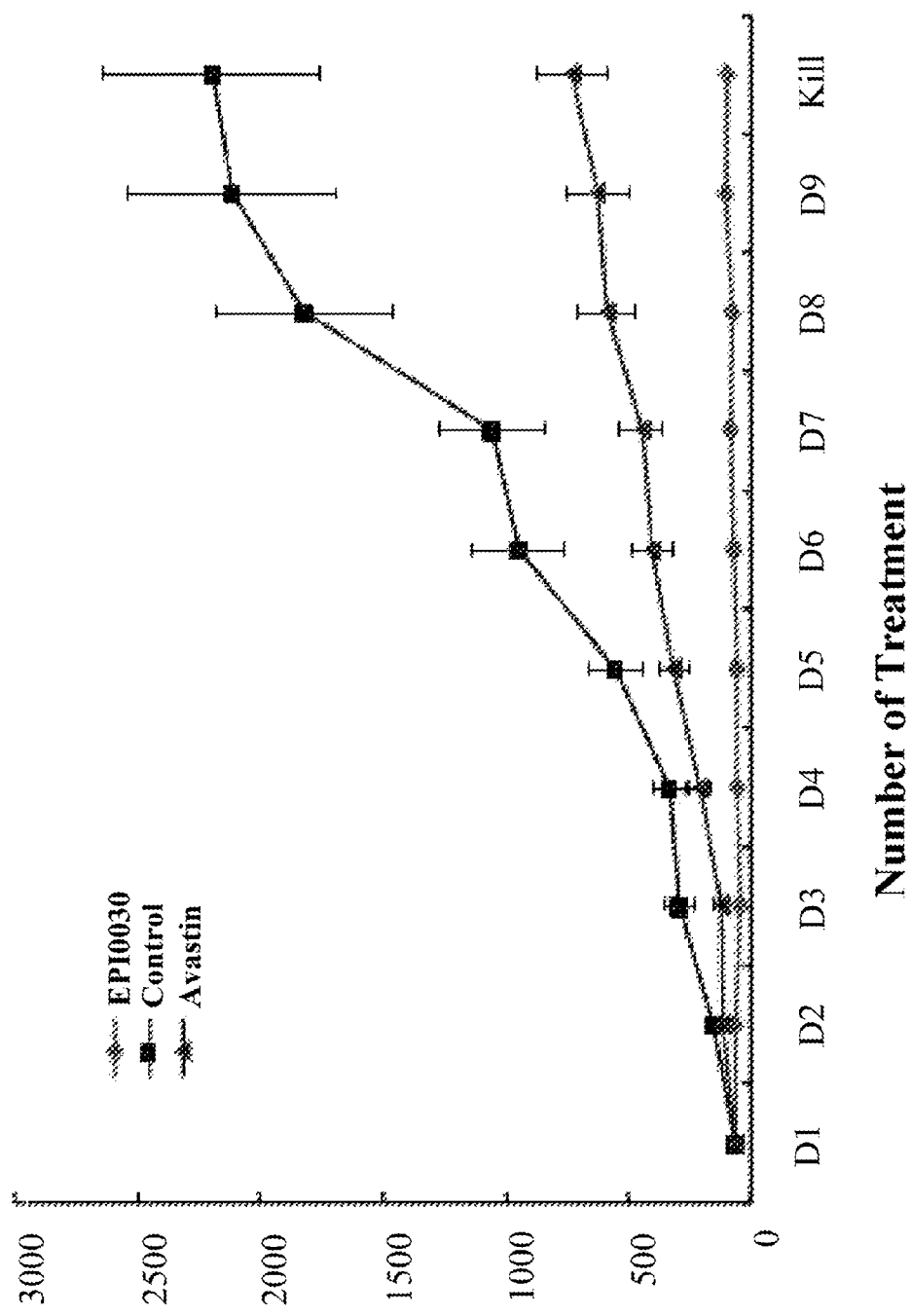
Figure 7:
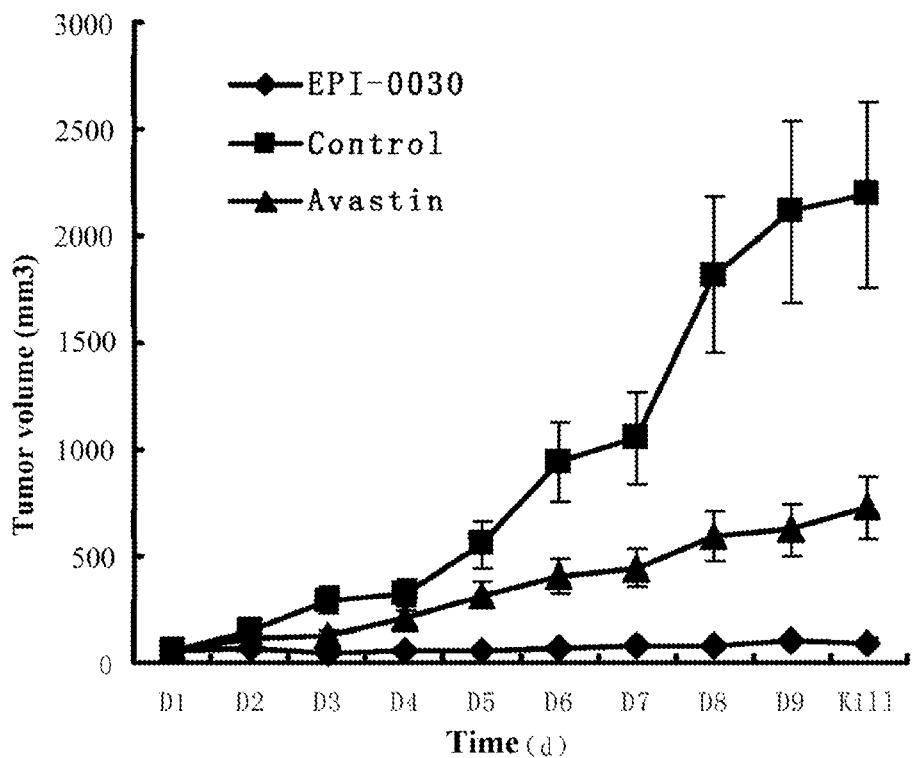
Figure 8:
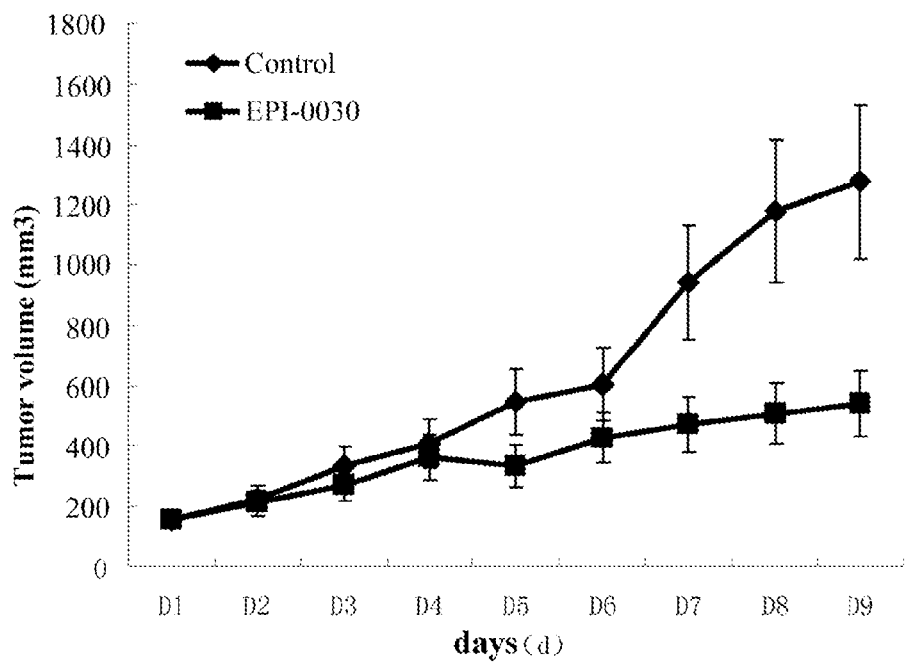

FIG. 6 shows the impact of 5 mg/kg EPI0030 and AVASTIN on the growth of HCT-116 tumor;

FIG. 7 shows the impact of 5 mg/kg EPI0030 and AVASTIN on the growth of NCI-H460 tumor;

FIG. 8 shows the impact of 1.5 mg/kg EPI0030 on the growth of NCI-H460 tumor.

DESCRIPTION OF THE SPECIFIC EMBODIMENTS

Example 1

Preparation of Hybrid Tumor Cell that Expresses Human VEGF165 Rabbit Monoclonal Antibody and Gene Clone Thereof Rabbit monoclonal clone antibody is prepared with the hybridoma technique. See U.S. Pat. No. 7,429,487, in particular Examples 1-4, for relevant experimental plans.

First, prepare IgG Fc-hVEGF-A (Human VEGF 165) fusion protein through the recombinant technology, wherein the IgG Fc sequence is the rabbit source. Clone the DNA sequence of IgG Fc-hVEGF-A into pTT5 plasmid, transiently transfect said plasmid into the HEK 293-6E cell line, cultivate cells in serum-free media, collect the supernatant, and purify the transiently expressed IgG Fc-hVEGF-A fusion protein that is purified with Protein A column.

Use the purified IgG Fc-hVEGF-A (as antigen component) to mix with the complete Freund's adjuvant in multi-point hypodermic injection for the first immunization on New Zealand rabbits, and then mix the purified protein with the incomplete Freund's adjuvant in hypodermic injection for enhanced immunization on the rabbits once per three weeks, and use the antigen plus PBS in intravenous injection on the rabbits for the final immunization 4 days prior to the spleen collection.

According to the method disclosed by the U.S. Pat. No. 7,429,487, fuse the rabbit spleen cell with the immortal HRGTP-B lymphocyte, 240E-W2 cell, which is homologous to the immunized spleen cell at a ratio of 2:1, cultivate in the HAT medium in a 96-well plate, then screen the hybridoma cells, and the obtained cell clones enter and bind with new IgG Fc-hVEGF-A for screening.

The identification and screening process comprises 2 positive clone screening steps: (1) immobilize the IgG Fc-hVEGF-A antigen on a 96-well ELISA plate, add the cloning and expression supernatant and incubate for 1 h, wash with PBS for 3 times, use the enzyme-labeled antibody to identify the cell clone supernatant having IgG Fc-hVEGF-A binding activity, and thereby obtain positive clones capable of directly binding with IgG Fc-hVEGF-A. (2) Subsequently, transfer the positive clones in Step (1) into a 24-well plate for cultivation to obtain more expression products. Immobilize the IgG Fc-VEGFR2 (KDR/Flk-1) extracellular region on a 96-well ELISA plate, add IgG Fc-hVEGF-A and the cloning and expression product to incubate together for 1 h, wash with PBS for 3 times, use the enzyme-labeled antibody to determine the content of IgG Fc-hVEGF-A so as to identify the inhibition of the clones on the VEGF-VEGFR2 binding activity, and thereby identify positive clones capable of blocking the VEGF-VEGFR2 binding.

The hybridoma cells of the screened positive clones undergo lysis, extract mRNA and obtain cDNA through reverse transcription. With said cDNA as the template, use the PCR method to amplify nucleotide sequences of the light chain and heavy chain variable domains of the rabbit IgG antibody, respectively, assay the heavy chain variable domain and the light chain variable domain, the encoded heavy chain variable domain comprising the parent sequence of SEQ ID NO: 1 (Ser Asn Asn Asp Val Met Cys Trp), the parent sequence of SEQ ID NO: 2 (Gly Cys Ile Met Thr Thr Asp Val Val Thr Glu Tyr Ala Asn Trp Ala Lys Ser), and the parent sequence of SEQ ID NO: 3 (Arg Asp Ser Val Gly Ser Pro Leu Met Ser Phe Asp Leu Trp), and the light chain variable domain comprising the parent sequence of SEQ ID NO: 4 (Gln Ala Ser Gln Ser Val Tyr Gly Asn Asn Glu Leu Ser), the parent sequence of SEQ ID NO: 5 (Arg Ala Ser Thr Leu Ala Ser), and the parent sequence of SEQ ID NO: 6 (Gly Gly Tyr Lys Ser Tyr Ser Asn Asp Gly Asn Gly). The light chain nucleotide sequences are cloned into the pTT5 plasmid. The nucleotide sequences of the heavy chain variable domain are cloned into the pTT5 plasmid that has a heavy chain constant domain. Co-transfect the light, heavy chain plasmids to the HEK 293-6E cell line, cultivate for 5 days, purify the supernatant with Protein A, and finally obtain the recombinant rabbit anti-human VEGF 165 monoclonal antibody. Use the above positive clone screening method to confirm the affinity of the expressed recombinant antibody.

Example 2

Preparation of the Humanized Rabbit Anti-VEGF165 Monoclonal Antibody According to the Present Invention See the U.S. Pat. No. 7,462,697, in particular its DETAILED DESCRIPTION OF PREFERRED EMBODIMENTS, for the humanization technique According to the technique disclosed by the U.S. Pat. No. 7,462,697, use human sequences VKI-2-1-(U)-A20_JK4 and VH3-1-3-3-21_JH4 as the reference sequences. 4 versions of VK and VH are obtained for each expressed rabbit anti-VEGF monoclonal antibody sequence after it is humanized. The light chain variable domain comprises VK-HZD1 (e.g. SEQ ID NO: 12), VK-HZD2 (e.g. SEQ ID NO: 14), VK-HZD5 (e.g. SEQ ID NO: 16) and VK-HZD6 (e.g. SEQ ID NO: 8); the heavy chain variable domain comprises VH-HZD1 (e.g. SEQ ID NO: 11), VH-HZD2 (e.g. SEQ ID NO: 13), VH-HZD5 (e.g. SEQ ID NO: 15) and VH-HZD6 (e.g. SEQ ID NO: 7). Compared with VK-HZD1, VK-HZD2 has 2 different residues in CDR1. VK-HZD1 and VK-HZD2 become VK-HZD5 and VK-HZD6, respectively, by adding two extra amino acid residues to the N terminal thereof. VH-HZD1 and VH-HZD2 have different residues at the $71^{st}$ position, the $71^{st}$ position of VH-HZD1 is K, while the $71^{st}$ position of VH-HZD2 is R. VK(H)-HZD1 and VK(H)-HZD 2 sequences comprise rabbit signal peptides, while VK(H)-HZD5 and VK(H)-HZD6 sequences comprise human signal peptides.

After artificial synthesis, clone the DNA sequences of the 4 versions of VK and VH into pTT5 plasmids having human CK sequences and human CH sequences, respectively, to express the antibody through human signal peptides. Co-transfect the above two plasmids to HEK 293-6E cell, and transiently express the humanized anti-VEGF antibody. According to the screening method in Example 1, select HZD-V6 clones have appropriate affinity as the clones to be used in the end, and the humanized anti-VEGF antibody expressed thereby is referred to as EPI0030, and its amino acid sequences are the heavy chain shown by SEQ ID NO: 9 and the light chain shown by SEQ ID NO: 10.

To increase the yield and obtain the cell line for industrial production, co-transfect expression plasmids having amino acid sequences of the heavy chain shown by SEQ ID NO: 9 and the light chain shown by SEQ ID NO: 10 into the Chinese hamster ovarian (CHO) cell line, which was deposited on Aug. 20, 2009 in CGMCC with the address at Datun Road, Chaoyang District, Beijing under the accession number of CGMCC No. 3233 under the terms of the Budapest Treaty.

Example 3

Figure 1:
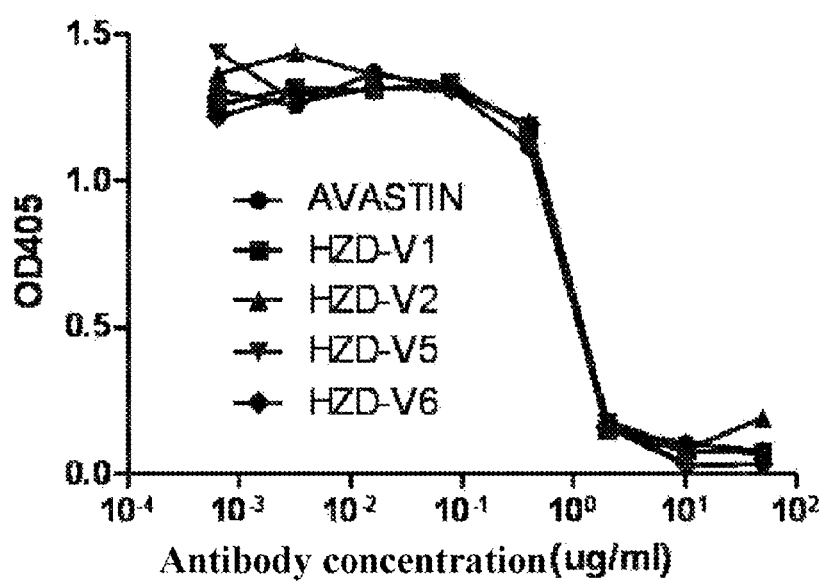
FIG. 1 shows competitive inhibition of the binding of VEGF and KDR by the recombinant antibody expressed through HZD-V1, HZD-V2, HZD-V5, and HZD-V6 clones.

Inspection of the Binding of the Monoclonal Antibody EPI0030 According to the Present Invention with VEGF The VEGF antibody binds with VEGF to block its binding with the receptor KDR and inhibit the VEGF signal channel. After 1:3 serial dilution of different recombinant antibodies (HZD-V1, HZD-V2, HZD-V5, HZD-V6) and AVASTIN (90 µg/ml-45 ng/ml), mix with IgG Fc-hVEGF (1 µg/ml), add the mixed antibody-VEGF complex into wells of a plate spread with IgG Fc-VEGFR2, and after adding the mouse anti-human VEGF antibody, detect through color development with goat anti-mouse IgG antibody -AP. The results show that the expressed recombinant antibodies have similar activity as AVASTIN in competitive inhibition of the binding of VEGF with KDR. The measurement results show that all antibodies expressed by HZD-V1, HZD-V2, HZD-V5 and HZD-V6 clones can block the binding of VEGF with KDR (see FIG. 1).

Referring to the above experimental approach, determine $IC_{50}$ values, i.e. median inhibitory concentrations, of EPI0030 and AVASTIN. The results are shown in FIG. 5, showing that EPI0030 and AVASTIN have similar competitive inhibition activity.

Use BIAcore-3000 to determine Kd of EPI0030 with VEGF. Immobilize human VEGF on the CM5 chip, inject EPI0030 and AVASTIN after 2 times serial dilution into the HBS-EP buffer solution with the flow rate of 30 ul/min. Kd is $k_{off}/k_{on}$. The dissociation constants of EPI0030 and AVASTIN with human VEGF are shown in Table 1, the dissociation constant of EPI0030 with VEGF is 0.485 nM, which is $\frac{1}{100}$ of that of AVASTIN, indicating that the binding capability of EPI0030 with VEGF is stronger than that of AVASTIN.

TABLE 1

Dissociation constants of EPI0030 and AVASTIN with human VEGF

| | Kd (nM) | | | |
| --- | --- | --- | --- | --- |
| | Experiment 1 | Experiment 2 | Average | STD |
| EPI0030 | 0.331 | 0.638 | 0.485 | 0.217 |
| AVASTIN | 61.9 | 33.8 | 47.9 | 19.9 |

Example 4

Characterization of the Monoclonal Antibody EPI0030 According to the Present Invention and Determination of the In Vitro Activity Thereof After purifying the EPI0030 antibody transiently expressed by HZD-V6 clone of the HEK 293-6E cell, perform associated quality analysis with the specific analysis items as follows:

A: Purity

Figure 2:
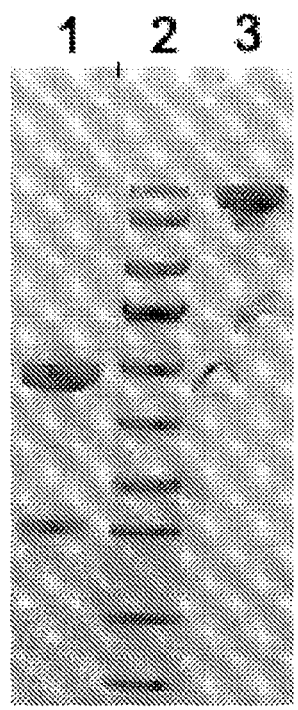
FIG. 2 shows the purity of EPI0030 antibody expressed by the HZD-V6 clone through SDS-PAGE.

Use SDS-PAGE (reducing and non-reducing) and SEC-HPLC to analyze purity with the results shown in FIG. 2 and FIG. 3, indicating that the purity of the EPI0030 antibody is greater than 98%, the polymer content is lower than 5%, main peak (retention time 10.572 min) area is greater than 95% of the total area (including peaks 1, 2 and 3 from left to right), and peaks 1 and 2 are polymers.

B: In Vitro Binding Activity

Use IgG Fc-hVEGF to spread the plate, use 1% BSA to seal, dilute the EPI0030 antibody and AVASTIN through 1:3 serial dilution at 8 grades (1 μg/ml-0.46 ng/ml), add the same into the wells spread with IgG Fc-hVEGF, add donkey anti-human IgG antibody for -AP detection. The results show that the EPI0030 antibody and AVASTIN have similar binding activity.

Use the ELISA method, including the IgG Fc-hVEGF direct binding method (see Example 1) and the KDR competitive binding method (Example 3). The results show that the binding of the EPI0030 antibody with VEGF is correlated to the inhibition of the binding of VEGF with KDR in terms of dosage, which are shown in FIG. 4 and FIG. 5.

Example 5

Detection of the In Vivo Activity of the Monoclonal Antibody EPI0030 According to the Present Invention At two weeks prior to the experiment, take one line of frozen human colon cancer HCT-116 cells and human non-small cell lung cancer NCI-H460 cells (about $1\times10^7$ cells) from the liquid nitrogen tank, and quickly place them into a 37° C. water bath to melt. Then, inoculate the cells into 75 $CM^2$ cell culture flasks with McCoy's 5A medium and DMEM medium that have been preheated to 37° C. and added with 10% fetal calf serum (purchased from GIBCO), respectively, subculture at 1:5 when the cells grow to 80% fusion rate, and subculture in vitro for three times in a row. When the total cell amount reaches the number required by inoculation, digest the cells with pancreatic enzyme and centrifuge, use PBS to wash the cells to remove serum, and at last, use serum-free, antibiotic-free McCoy's 5A medium and DMEM medium to adjust the cell densities of the processed human colon cancer HCT-116 cells and human non-small cell lung cancer NCI-H460 cells to $5\times10^7$/ml, respectively, place the cell suspension on ice, inoculate to the ventral part of 6-8 week old nude mice, inoculate 0.1 ml to each mouse, i.e. $5\times10^6$ cells/mouse. Use a vernier caliper to measure the tumor diameter of the nude mice every 2 days, when tumors of all mice grow to 100 $mm^3$-300 $mm^3$, select those with tumor volume SD<⅓, randomly separate them into 5 groups with 6 per group. The human colon cancer HCT-116 model groups are the model control group (1 group), 5 mg/kg AVASTIN (1 group) and 5 mg/kg EPI-0030 (1 group), and use physiological saline to dilute AVASTIN and EPI-0030 to 0.5 mg/ml. The human non-small cell lung cancer NCI-H460 model groups are the model control group (1 group), 5 mg/kg AVASTIN (1 group) and 1.5 mg/kg, 5 mg/kg EPI-0030 (2 groups), and use physiological saline to dilute AVASTIN and EPI-0030 to 0.5 mg/ml and 0.15 mg/ml. For the drug administration groups, 0.2 ml AVASTIN and EPI-0030 are administrated through intraperitoneal injection, respectively, once at 1, 3, and 5 days of each week, and 0.2 ml physiological saline is administrated to the model control groups at the same time and via the same way, and the administration is continued for 3 weeks (21 days, a total of 9 times).

Measure the maximum diameter a and the minimum diameter b of the nude mice's tumor nodules, calculate the tumor volume according to the equation, $V=0.5\times a\times b^2$, and use the relative tumor growth rate, T/C %, as the index to evaluate the healing efficacy.

The results show that in the human colon cancer HCT-116 model, the tumor inhibition rates of EPI-0030 and AVASTIN in the 5 mg/kg group are 65.7% and 15.7%, respectively (see FIG. 6). In the human non-small cell lung cancer NCI-H460 model, the tumor inhibition rates of EPI-0030 and AVASTIN are 95.5% and 66.7%, respectively (see FIG. 7); and in the 1.5 mg/kg group, the tumor inhibition rate of EPI-0030 is 57.6% (see FIG. 8). The results show that EPI-0030 has remarkable capability to inhibit tumor growth.

By referring to AVASTIN's clinical indications, choose xenograft tumor models of human colon cancer HCT-116 and human non-small cell lung cancer NCI-H460 in nude mice to verify the inhibition of human colon cancer and human non-small cell lung cancer by EPI-0030, proving that EPI-0030 has remarkable inhibition of xenograft tumors of human colon cancer and human non-small cell lung cancer. In the models, EPI-0030 has stronger tumor inhibition activity than AVASTIN.

The above description only discloses preferred embodiments of the present invention. It should be noted that to those skilled in the art, a number of improvements and modifications may be made without departing from the principles of the present invention. All these improvements and modifications shall be encompassed by the protection scope of the present invention.

The invention claimed is:

1. A monoclonal antibody or an antigen-binding domain thereof, wherein its heavy chain variable domain comprises amino acid sequences as shown in SEQ ID NO:1, SEQ ID NO:2 and SEQ ID NO:3, and its light chain variable domain comprises amino acid sequences as shown in SEQ ID NO:4, SEQ ID NO:5 and SEQ ID NO:6.

2. The monoclonal antibody or antigen-binding domain of claim 1, wherein said monoclonal antibody is a single-strand antibody, double-strand antibody, chimeric antibody, or humanized antibody.

3. The monoclonal antibody or antigen-binding domain of claim 1, wherein the amino acid sequence of its heavy chain variable domain is shown by SEQ ID NO:7.

4. The monoclonal antibody or antigen-binding domain of claim 1, wherein the amino acid sequence of its light chain variable domain is shown by SEQ ID NO:8.

5. The monoclonal antibody or antigen-binding domain of claim 1, wherein its heavy chain amino acid sequence is shown by SEQ ID NO:9.

6. The monoclonal antibody or antigen-binding domain of claim 1, wherein its light chain amino acid sequence is shown by SEQ ID NO:10.

7. The monoclonal antibody or antigen-binding domain of claim 1, wherein it is produced by the cell line deposited under the accession number of CGMCC No. 3233.

8. A method for treating a VEGF-associated disease, comprising administering to a patient in need thereof an effective amount of the monoclonal antibody or antigen-binding domain of claim 1.

9. The method of claim 8, wherein said VEGF-associated disease is a tumor or age-related macular degeneration (AMD).

10. The method of claim 8, wherein the VEGF-associated disease is colon cancer.

11. A pharmaceutical composition, wherein it comprises an effective amount of the monoclonal antibody or antigen-binding domain of claim 1 and a pharmaceutically acceptable carrier.

12. A reagent, kit or chip, comprising the monoclonal antibody or antigen-binding domain of claim 1.

13. A cell line deposited in CGMCC under the accession number of CGMCC No. 3233.

* * * * *

SEQUENCE LISTING

```
<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: Heavy chain variable region CDR1

<400> SEQUENCE: 1
```

```
Ser Asn Asn Asp Val Met Cys Trp
1               5

<210> SEQ ID NO 2
<211> LENGTH: 18
<212> TYPE: PRT
<213> ORGANISM: Artificial Sequence
<220> FEATURE:
<223> OTHER INFORMATION: Heavy chain variable region CDR2

<400> SEQUENCE: 2

Gly Cys Ile Met Thr Thr Asp Val Val Thr Glu Tyr Ala Asn Trp Ala
1               5                   10                  15

Lys Ser

<210> SEQ ID NO 3
<211> LENGTH: 14
<212> TYPE: PRT
<213> ORGANISM: Artificial Sequence
<220> FEATURE:
<223> OTHER INFORMATION: Heavy chain variable region CDR3

<400> SEQUENCE: 3

Arg Asp Ser Val Gly Ser Pro Leu Met Ser Phe Asp Leu Trp
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Light chain variable region CDR1

<400> SEQUENCE: 4

Gln Ala Ser Gln Ser Ile Tyr Asn Asn Asn Glu Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Light chain variable region CDR2

<400> SEQUENCE: 5

Arg Ala Ser Thr Leu Ala Ser
1               5

<210> SEQ ID NO 6
<211> LENGTH: 12
<212> TYPE: PRT
<213> ORGANISM: Artificial Sequence
<220> FEATURE:
<223> OTHER INFORMATION: Light chain variable region CDR3

<400> SEQUENCE: 6

Gly Gly Tyr Lys Ser Tyr Ser Asn Asp Gly Asn Gly
1               5                   10

<210> SEQ ID NO 7
<211> LENGTH: 141
<212> TYPE: PRT
<213> ORGANISM: Artificial Sequence
<220> FEATURE:
<223> OTHER INFORMATION: Heavy chain variable region
```

-continued

<400> SEQUENCE: 7

```
Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Ser Phe
        35                  40                  45

Ser Asn Asn Asp Val Met Cys Trp Val Arg Gln Ala Pro Gly Lys Gly
    50                  55                  60

Leu Glu Trp Ile Gly Cys Ile Met Thr Thr Asp Val Val Thr Glu Tyr
65                  70                  75                  80

Ala Asn Trp Ala Lys Ser Arg Phe Thr Val Ser Arg Asp Ser Ala Lys
                85                  90                  95

Asn Ser Val Tyr Leu Gln Met Asn Ser Leu Arg Ala Glu Asp Thr Ala
            100                 105                 110

Val Tyr Phe Cys Ala Arg Asp Ser Val Gly Ser Pro Leu Met Ser Phe
        115                 120                 125

Asp Leu Trp Gly Pro Gly Thr Leu Val Thr Val Ser Ser
    130                 135                 140
```

<210> SEQ ID NO 8
<211> LENGTH: 134
<212> TYPE: PRT
<213> ORGANISM: Artificial Sequence
<220> FEATURE:
<223> OTHER INFORMATION: Light chain variable region

<400> SEQUENCE: 8

```
Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
            20                  25                  30

Leu Ser Ala Ser Val Gly Asp Arg Val Thr Ile Asn Cys Gln Ala Ser
        35                  40                  45

Gln Ser Ile Tyr Asn Asn Asn Glu Leu Ser Trp Tyr Gln Gln Lys Pro
    50                  55                  60

Gly Lys Pro Pro Lys Leu Leu Ile Tyr Arg Ala Ser Thr Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Val Ala Thr Tyr Tyr Cys
            100                 105                 110

Gly Gly Tyr Lys Ser Tyr Ser Asn Asp Gly Asn Gly Phe Gly Gly Gly
        115                 120                 125

Thr Lys Val Glu Ile Lys
    130
```

<210> SEQ ID NO 9
<211> LENGTH: 471
<212> TYPE: PRT
<213> ORGANISM: Artificial Sequence
<220> FEATURE:
<223> OTHER INFORMATION: Heavy chain

<400> SEQUENCE: 9

```
Met Glu Leu Gly Leu Arg Trp Val Phe Leu Val Ala Ile Leu Glu Gly
1               5                   10                  15
```

```
Val Gln Cys Glu Val Gln Leu Val Glu Ser Gly Gly Leu Val Lys
             20                  25                  30

Pro Gly Gly Ser Leu Arg Leu Ser Cys Ala Ala Ser Gly Phe Ser Phe
             35                  40                  45

Ser Asn Asp Val Met Cys Trp Val Arg Gln Ala Pro Gly Lys Gly
 50                  55                  60

Leu Glu Trp Ile Gly Cys Ile Met Thr Thr Asp Val Val Thr Glu Tyr
65                   70                  75                  80

Ala Asn Trp Ala Lys Ser Arg Phe Thr Val Ser Arg Asp Ser Ala Lys
                 85                  90                  95

Asn Ser Val Tyr Leu Gln Met Asn Ser Leu Arg Ala Glu Asp Thr Ala
                100                 105                 110

Val Tyr Phe Cys Ala Arg Asp Ser Val Gly Ser Pro Leu Met Ser Phe
            115                 120                 125

Asp Leu Trp Gly Pro Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
    355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
```

```
            435                 440                 445
Cys Ser Val Met His Glu Ala Leu His Asn His Tyr Thr Gln Lys Ser
    450                 455                 460
Leu Ser Leu Ser Pro Gly Lys
465             470

<210> SEQ ID NO 10
<211> LENGTH: 241
<212> TYPE: PRT
<213> ORGANISM: Artificial Sequence
<220> FEATURE:
<223> OTHER INFORMATION: Light chain

<400> SEQUENCE: 10

Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
                20                  25                  30

Leu Ser Ala Ser Val Gly Asp Arg Val Thr Ile Asn Cys Gln Ala Ser
            35                  40                  45

Gln Ser Ile Tyr Asn Asn Glu Leu Ser Trp Tyr Gln Gln Lys Pro
    50                  55                  60

Gly Lys Pro Lys Leu Leu Ile Tyr Arg Ala Ser Thr Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Val Ala Thr Tyr Tyr Cys
            100                 105                 110

Gly Gly Tyr Lys Ser Tyr Ser Asn Asp Gly Asn Gly Phe Gly Gly Gly
        115                 120                 125

Thr Lys Val Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 11
<211> LENGTH: 140
<212> TYPE: PRT
<213> ORGANISM: Artificial Sequence
<220> FEATURE:
<223> OTHER INFORMATION: HZD1 Heavy chain variable region

<400> SEQUENCE: 11

Met Glu Thr Gly Leu Arg Trp Leu Leu Leu Val Ala Val Leu Lys Ser
1               5                   10                  15

Val Gln Cys Gln Gln Leu Val Glu Ser Gly Gly Gly Leu Val Lys Pro
```

```
                    20                  25                  30
Gly Gly Ser Leu Arg Leu Ser Cys Ala Ala Ser Gly Phe Ser Phe Ser
                35                  40                  45

Asn Asn Asp Val Met Cys Trp Val Arg Gln Ala Pro Gly Lys Gly Leu
        50                  55                  60

Glu Trp Ile Gly Cys Ile Met Thr Thr Asp Val Thr Glu Tyr Ala
 65                  70                  75                  80

Asn Trp Ala Lys Ser Arg Phe Thr Val Ser Lys Asp Ser Ala Lys Asn
                85                  90                  95

Ser Val Tyr Leu Gln Met Asn Ser Leu Arg Ala Glu Asp Thr Ala Val
            100                 105                 110

Tyr Phe Cys Ala Arg Asp Ser Val Gly Ser Pro Leu Met Ser Phe Asp
            115                 120                 125

Leu Trp Gly Pro Gly Thr Leu Val Thr Val Ser Ser
            130                 135                 140

<210> SEQ ID NO 12
<211> LENGTH: 134
<212> TYPE: PRT
<213> ORGANISM: Artificial Sequence
<220> FEATURE:
<223> OTHER INFORMATION: HZD1 Light chain variable region

<400> SEQUENCE: 12

Met Asp Thr Arg Ala Pro Thr Gln Leu Leu Gly Leu Leu Leu Leu Trp
 1               5                  10                  15

Leu Pro Gly Ala Arg Cys Ala Leu Gln Met Thr Gln Ser Pro Ser Ser
                20                  25                  30

Leu Ser Ala Ser Val Gly Asp Arg Val Thr Ile Asn Cys Gln Ala Ser
            35                  40                  45

Gln Ser Val Tyr Gly Asn Asn Glu Leu Ser Trp Tyr Gln Gln Lys Pro
        50                  55                  60

Gly Lys Pro Pro Lys Leu Leu Ile Tyr Arg Ala Ser Thr Leu Ala Ser
 65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Val Ala Thr Tyr Tyr Cys
            100                 105                 110

Gly Gly Tyr Lys Ser Tyr Ser Asn Asp Gly Asn Gly Phe Gly Gly Gly
            115                 120                 125

Thr Lys Val Glu Ile Lys
            130

<210> SEQ ID NO 13
<211> LENGTH: 140
<212> TYPE: PRT
<213> ORGANISM: Artificial Sequence
<220> FEATURE:
<223> OTHER INFORMATION: HZD2 Heavy chain variable region

<400> SEQUENCE: 13

Met Glu Thr Gly Leu Arg Trp Leu Leu Leu Val Ala Val Leu Lys Ser
 1               5                  10                  15

Val Gln Cys Gln Gln Leu Val Glu Ser Gly Gly Gly Leu Val Lys Pro
                20                  25                  30

Gly Gly Ser Leu Arg Leu Ser Cys Ala Ala Ser Gly Phe Ser Phe Ser
            35                  40                  45
```

```
Asn Asn Asp Val Met Cys Trp Val Arg Gln Ala Pro Gly Lys Gly Leu
    50                  55                  60

Glu Trp Ile Gly Cys Ile Met Thr Thr Asp Val Val Thr Glu Tyr Ala
65                  70                  75                  80

Asn Trp Ala Lys Ser Arg Phe Thr Val Ser Arg Asp Ser Ala Lys Asn
                85                  90                  95

Ser Val Tyr Leu Gln Met Asn Ser Leu Arg Ala Glu Asp Thr Ala Val
            100                 105                 110

Tyr Phe Cys Ala Arg Asp Ser Val Gly Ser Pro Leu Met Ser Phe Asp
            115                 120                 125

Leu Trp Gly Pro Gly Thr Leu Val Thr Val Ser Ser
    130                 135                 140

<210> SEQ ID NO 14
<211> LENGTH: 134
<212> TYPE: PRT
<213> ORGANISM: Artificial Sequence
<220> FEATURE:
<223> OTHER INFORMATION: HZD2 Light chain variable region

<400> SEQUENCE: 14

Met Asp Thr Arg Ala Pro Thr Gln Leu Leu Gly Leu Leu Leu Leu Trp
1               5                   10                  15

Leu Pro Gly Ala Arg Cys Ala Leu Gln Met Thr Gln Ser Pro Ser Ser
            20                  25                  30

Leu Ser Ala Ser Val Gly Asp Arg Val Thr Ile Asn Cys Gln Ala Ser
        35                  40                  45

Gln Ser Ile Tyr Asn Asn Glu Leu Ser Trp Tyr Gln Gln Lys Pro
    50                  55                  60

Gly Lys Pro Pro Lys Leu Leu Ile Tyr Arg Ala Ser Thr Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Val Ala Thr Tyr Tyr Cys
            100                 105                 110

Gly Gly Tyr Lys Ser Tyr Ser Asn Asp Gly Asn Gly Phe Gly Gly Gly
            115                 120                 125

Thr Lys Val Glu Ile Lys
    130

<210> SEQ ID NO 15
<211> LENGTH: 141
<212> TYPE: PRT
<213> ORGANISM: Artificial Sequence
<220> FEATURE:
<223> OTHER INFORMATION: HZD5 Heavy chain variable region

<400> SEQUENCE: 15

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Ser Phe
        35                  40                  45

Ser Asn Asn Asp Val Met Cys Trp Val Arg Gln Ala Pro Gly Lys Gly
    50                  55                  60

Leu Glu Trp Ile Gly Cys Ile Met Thr Thr Asp Val Val Thr Glu Tyr
65                  70                  75                  80
```

```
Ala Asn Trp Ala Lys Ser Arg Phe Thr Val Ser Lys Asp Ser Ala Lys
                85                  90                  95

Asn Ser Val Tyr Leu Gln Met Asn Ser Leu Arg Ala Glu Asp Thr Ala
            100                 105                 110

Val Tyr Phe Cys Ala Arg Asp Ser Val Gly Ser Pro Leu Met Ser Phe
        115                 120                 125

Asp Leu Trp Gly Pro Gly Thr Leu Val Thr Val Ser Ser
    130                 135                 140

<210> SEQ ID NO 16
<211> LENGTH: 134
<212> TYPE: PRT
<213> ORGANISM: Artificial Sequence
<220> FEATURE:
<223> OTHER INFORMATION: HZD5 Light chain variable region

<400> SEQUENCE: 16

Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
                20                  25                  30

Leu Ser Ala Ser Val Gly Asp Arg Val Thr Ile Asn Cys Gln Ala Ser
            35                  40                  45

Gln Ser Val Tyr Gly Asn Asn Glu Leu Ser Trp Tyr Gln Gln Lys Pro
    50                  55                  60

Gly Lys Pro Pro Lys Leu Leu Ile Tyr Arg Ala Ser Thr Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Val Ala Thr Tyr Tyr Cys
            100                 105                 110

Gly Gly Tyr Lys Ser Tyr Ser Asn Asp Gly Asn Gly Phe Gly Gly Gly
            115                 120                 125

Thr Lys Val Glu Ile Lys
    130
```